United States Patent [19]

Schechter

[11] Patent Number: 4,911,161

[45] Date of Patent: Mar. 27, 1990

[54] CAPSULECTOMY CUTTING APPARATUS

[75] Inventor: Alan M. Schechter, Los Alamitos, Calif.

[73] Assignee: Noetix, Inc., Indianapolis, Ind.

[21] Appl. No.: 43,849

[22] Filed: Apr. 29, 1987

[51] Int. Cl.⁴ ............................................. A61F 17/32
[52] U.S. Cl. ................................................... 606/171
[58] Field of Search ..................... 128/303.1, 305, 751, 128/755, 306–319; 206/229, 230, 352, 364, 365, 569, 571; 604/163, 171, 192, 263

[56] References Cited

U.S. PATENT DOCUMENTS

| 3,055,364 | 9/1962 | Myersen et al. | 604/192 |
| 3,794,040 | 2/1974 | Balamuth | 128/303.1 |
| 3,809,093 | 5/1974 | Abraham | 128/305 |
| 3,937,222 | 2/1976 | Banko | 128/305 |
| 4,570,632 | 2/1986 | Woods | 128/305 |
| 4,705,037 | 11/1987 | Peyman et al. | 128/305 |
| 4,706,669 | 11/1987 | Schlegel | 128/305 |

FOREIGN PATENT DOCUMENTS

| 3434930 | 4/1986 | Fed. Rep. of Germany | 128/305 |
| 114998 | 6/1925 | Switzerland | 128/305 |

OTHER PUBLICATIONS

English translation of Swiss patent 114,998 to Reiniger et al., May 1926.

Primary Examiner—Max Hindenburg
Attorney, Agent, or Firm—Alton W. Payne

[57] ABSTRACT

A capsulectomy apparatus which comprises a console, a handpiece and a needle. The handpiece operates from a vibrating transducer which drives a rod within the sleeve of the needle for actively engageing the anterior lens capsule which is to be severed. The head of the needle which engages and cuts the anterior lens capsule of the eye has a specific angular relationship with the rod within the needle. Also, the cutting edges and surfaces associated with the head of the needle have a specific configuration for enhancing the cutting quality of the apparatus. The needle is disposable and specifically configured to be removeably affixed to the handpiece.

11 Claims, 5 Drawing Sheets

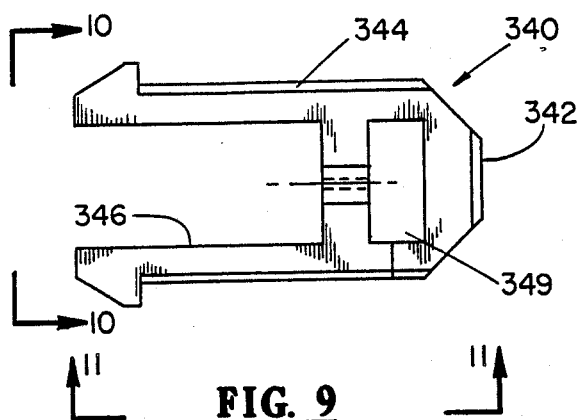
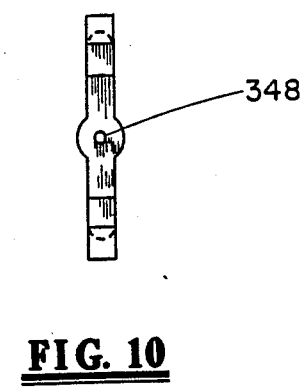
FIG. 9     FIG. 10
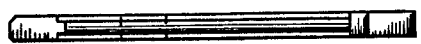
FIG. 11
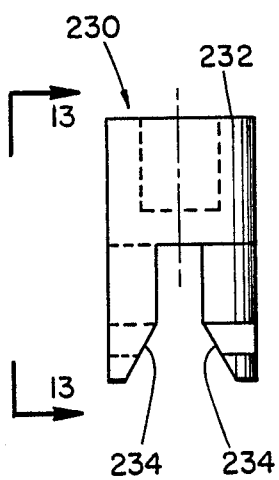
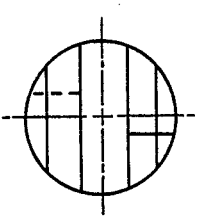
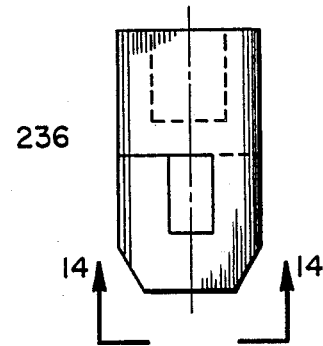
FIG. 12     FIG. 14     FIG. 13
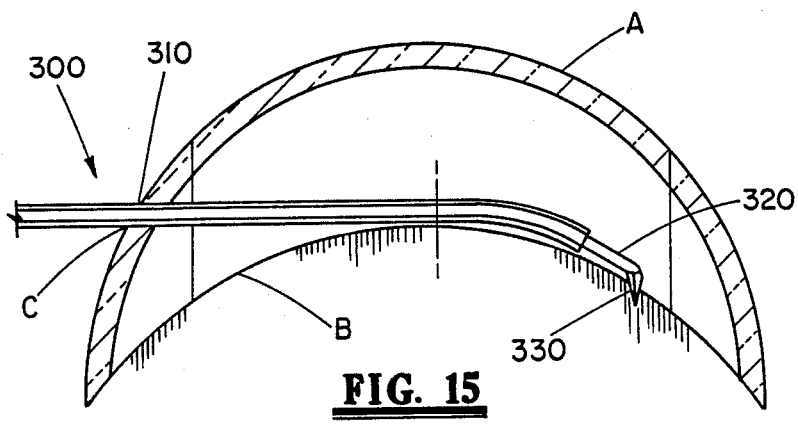
FIG. 15

CAPSULECTOMY CUTTING APPARATUS

FIELD OF THE INVENTION

The present invention relates generally to ophthalmic surgery. Specifically, the present invention relates to an electromechanical membrane/tissue cutter-capsulectomy apparatus for continuously and smoothly severing portions of the anterior lens capsule of the human eye.

BACKGROUND OF THE INVENTION

With the increased rate of success of ophthalmic surgery, the need has grown for surgical devices and methods which further enhance surgical techniques. With the advent of varied and different surgical techniques, new devices and methods have been advocated and new successes have been recorded. Specifically, the need to enhance the methods and procedures for performing the anterior capsulectomy during extracapsular surgery have become critical to the success of the surgery. Numerous methods are currently used and numerous apparatus are currently employed.

Many surgical and diagnostic procedures are currently being performed manually. In many instances, the clinician has difficulty performing the procedure or evaluating the condition using the manual method.

Automation of the device goes far beyond the use of electromechanical or other energy forms to drive the instrument. Automation implies the development of a more sophisticated device that significantly improves the procedure as it is currently performed.

The development of an automated device requires the use of new techniques, and not merely using a new device the old way. Significant patient benefits will result by enabling the clinician to be more effective and efficient. This includes: reduced trauma, better postoperative rehabilitation, and more quantitative results.

The anterior capsule is a cellophane-like membrane covering the anterior surface of the lens. It is continuous with the posterior capsule, a cellophane-like membrane behind the lens. The human lens is encapsulated by this membrane. In order for a cataract (opacified lens) to be removed in an extracapsular extraction procedure, the anterior capsule must be opened to allow for instrumentation to enter "the bag" and removal of the nucleus and cortical material. Various techniques and principles have been devised to cut or tear the anterior capsule. For example, some well known techniques include the "Christmas tree," the "Beer-can," and various modifications of these techniques. An excellent review of the methods and complications can be found in *Phacoemulsification and Asperation of Cataracts*, J. M. Emery and J. H. Little, Eds., Chapter 10, (1979), C. V. Mosby Co.

The anterior capsulectomy is generally recognized as the most difficult step in the cataract procedure. Numerous articles have appeared in *Ocular Surgical News and Ophthalmology Times* on the anterior capsulectomy procedure. Many surgeons have tremendous problems with the capsulectomy procedure even through they are quite proficient in the other steps in the procedure.

A poorly performed anterior capsulectomy significantly increases the difficulty in performing the subsequent steps in the procedure and the probability of operative complications. Complications resulting from a poor capsulectomy include: zonular stress with subsequent breakage of the posterior capsule, difficulty in nucleus expression, and large capsular tags preventing efficient cortical removal including increased operative time and probability of vitreous loss. A poor capsulectomy also prevents placement of an intraocular lens (IOL) in the capsular bag due to ill-defined capsular structures. Many journal articles, some referenced herein, substantiate the difficulty in performing the procedures and the ensuing complications from a poorly performed technique. The articles also suggests surgical techniques to improve the results and reduce the difficulty in the subsequent steps.

As a result of the difficulties and complications cited, a definitive need exits for a device and technique to perform an efficient, effective, and efficacious anterior capsulectomy. Such a device should simplify the procedure and enable the surgeon to perform the capsulectomy, and the subsequent steps, more quickly and effectively.

Some of these prior used methods include manual and mechanical techniques for severing the anterior lens capsule of the eye to perform the capsulectomy. For example, a mechanical device was disclosed by Henry M. Clayman and Jean-Marie Parel in the *American Intra-Ocular Implant Society Journal*, Volume 10, Fall 1984, pp. 479-482. The Clayman/Parel paper, entitled "The Capusule Coupeur for Automated Anterior Capsulectomy," describes a mechanical automated anterior capsulectomy device. The Clayman/Parel device operated from a power source and provided a rotating cutting tip. The rotating cutting tip extended from the end of a tube and rotated orthogonal to the center axis of the tube. The cutting edge caused the incision of the anterior lens capsule of the eye.

Additional devices are known for performing the capsulectomy. For example, Sharp Point, Inc. has a manual device which utilizes a rigid rod with a freely rotating cutting member for cutting the eye. As the cutting member at the end of the rod is moved in a circular path across the tissue, the cutting edge of the "nail-like" cutting member cuts the lens of the eye along the path traversed. Other manual devices are known in the art, for example, cystotomes and gauge vent needles. Also, an ultrasonic driven uptotome is known in the art.

In all of the prior known devices, it is difficult to cleanly cut the capsule without leaving residual "tags" or tears in the capsule. Also, prior known devices either cause sufficient drag on the capsule to rock the nucleus of the lens or to place stress on the zonular structure. All of these problems tend to create undesirable foundations for intraocular lens placement or other surgical complications.

It is, therefore, a feature of the present invention to provide a capsulectomy apparatus which facilitates a continuous smooth, curvilinear cut.

Another feature of the present invention is to provide a capsulectomy apparatus which does not rock the nucleus of the lens.

Yet another feature of the present invention is to provide a capsulectomy apparatus for facilitating a continuous, smooth, curvilinear cut of the anterior lens capsule while reducing zonular stress and ultimately eliminating zonular dialysis.

Still another feature of the present invention is to provide a capsulectomy apparatus which provides a cleanly cut capsule.

Yet still another feature of the present invention is to provide a capsulectomy apparatus that eliminates residual tags of the anterior capsule.

A further feature of the present invention is to provide a capsulectomy apparatus which easily cuts any desired capsular pattern, at any location, and of any size.

Yet further, an additional feature of the present invention is to provide a capsulectomy apparatus which provides a superior foundation for "in-the-bag" lens placement.

Yet another feature of the present invention is to provide a capsulectomy apparatus which minimizes the shear forces associated with capsular tears.

Yet still another feature of the present invention is to provide a capsulectomy apparatus which facilitates a continuous, smooth, curvilinear cut for the anterior capsule.

An additional feature of the present invention is to provide a capsulectomy apparatus which provides a free-flowing anterior capsule button.

Additional features and advantages of the invention will be setforth in part in the description which follows, and in part will become apparent from the description, or may be learned by practice of the invention. The features and advantages of the invention may be realized by means of the combinations and steps particularly pointed out in the appended claims.

SUMMARY OF THE INVENTION

To achieve the foregoing objects, features, and advantages and in accordance with the purpose of the invention as embodied and broadly described herein, a capsulectomy apparatus is provided for facilitating a continuous, smooth, curvilinear, stress-free, tag-free, free-floating cut of the anterior capsule which comprises a console for providing power for and control of the capulatomy apparatus, a handpiece in operative association with the console, and a disposable needle in direct association with the handpiece for entering the eye and initiating the capsulectomy.

More particularly, the handpiece of the present invention utilizes a magnetically driven transducer for providing longitudinal movement to the cutting portion of the needle. The handpiece contains a driver end which remotely engages the magnetically driven transducer for activating a toggle which directly engages the cutting portion of the needle.

The disposable needle of the present invention comprises a sleeve, a rod and a head having a plurality of cutting edges. The rod is driven back and forth or oscillated in the sleeve such that the cutting head provides a continuous, smooth, tag-free, free-floating clean cut of the capsule by the plurality of cutting edges. In one embodiment the cutting head is a pyramid-like configuration. The pyramid-like cutting head resembles a polyhedron. However, the typically planar faces of the polyhedral, pyramid-like structure are concaved. Preferably, the radius of curvature associated with the concaved surfaces of the polyhedral structure is less than approximately 0.05 inches. In one preferred embodiment of the capsulectomy apparatus of the present invention, the cutting head resembles a four-sided pyramid with concaved walls having a radius of curvature of approximately 0.037 inches. Both the number of sides associated with the polyhedrical structure and the radius of curvature associated with each wall thereof can be varied to achieve the efficacies desired. Further, the angle of the head with respect to the rod is approximately 70 degrees. However, the angle of the head with respect to the rod can vary from approximately 60 degrees to approximately 120 degrees. The disposable needle locks into the handpiece by attachment of the male to the female end as illustrated in the drawings.

BRIEF DESCRIPTION OF THE DRAWINGS

The accompanying drawings which are incorporated in and constitute a part of the specification, illustrate a preferred embodiment of the invention and together with the general description of the invention given above and the detailed description of the preferred embodiment given below, serve to explain the principles of the invention.

FIG. 9 is a sectional view of a preferred embodiment of the toggle apparatus associated with the end/locking portion of the capsulectomy apparatus of the present invention;

FIG. 10 is a cross-sectional view of the toggle apparatus taken along sectional 10—10 in FIG. 9;

FIG. 11 is a cross-sectional view of the toggle apparatus taken along section line 11—11 in FIG. 9;

FIG. 12 is a sectional view of a preferred embodiment of the female actuator utilized with the needle of the capsulectomy apparatus of the present invention;

FIG. 13 is a cross-sectional view of the female actuator taken along the section line 13—13 in FIG. 12;

FIG. 14 is a cross-sectional view of the female actuator taken along the section line 14—14 in FIG. 13;

FIG. 15 is an illustration of a preferred embodiment of the needle of the capsulectomy apparatus of the present invention while inserted into the eye and engaged with the anterior lens capsule;

The above general description and the following detailed description are merely illustrative of the generic invention, and additional modes, advantages, and particulars of this invention will be readily suggested to those skilled in the art without departing from the spirit and scope of the invention.

DETAILED DESCRIPTION OF THE PREFERRED EMBODIMENT

Reference will now be made in detail to the present preferred embodiment of the invention as described in the accompanying drawings.

Figure 1:
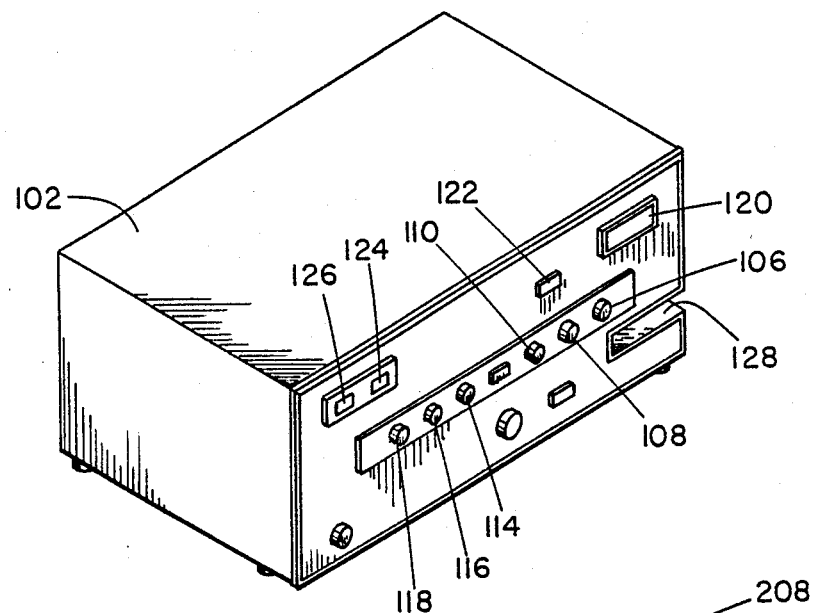
FIG. 1 is a view of a preferred embodiment of the console of the capsulectomy apparatus of the present invention.

In FIG. 1 there is shown an illustration of a console 100 associated with the capsulectomy apparatus of the present invention. The console 100 is emcopassed by the housing 102. On the front of the housing 102 is the panel 104. The panel 104 has indicators for determining the accurate operation of the capsulectomy apparatus of the present invention. On panel 104 are the cutting indicator 106, the irrigation indicator 108, the fault indicator 110, the test button 112, the ready indicator 114, the needle indicator 116, the handpiece indicator 118, the timer 120, the reset 122, the battery charge indicator 124, and the battery low indicator 126, Also, illustrated in FIG. 1 is the irrigation solenoid 128.

Figure 2:
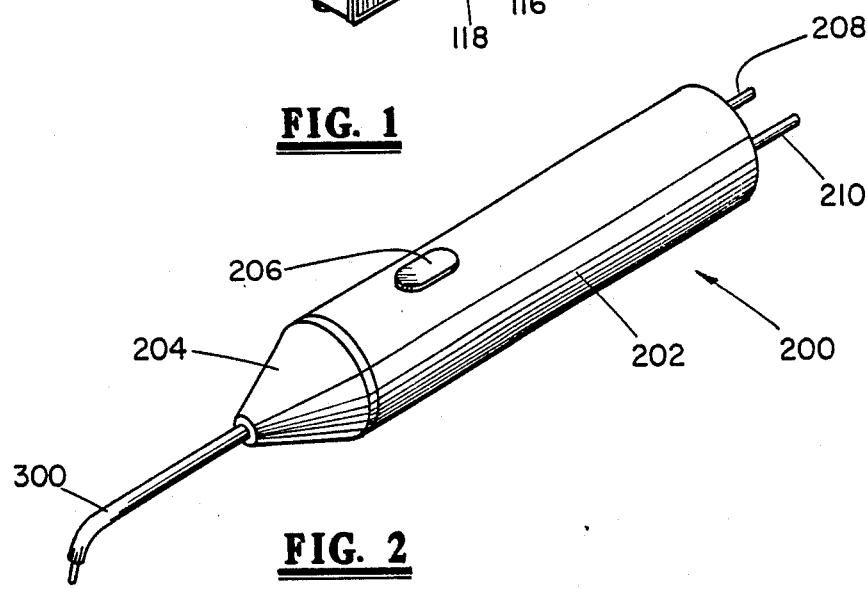
FIG. 2 is a view of a preferred embodiment of the handpiece which operates in conjunction with the console of the capsulectomy apparatus of the present invention.

FIG. 2 is an illustration of the handpiece 200 of the capsulectomy apparatus of the present invention. Also illustrated in FIG. 2 is the disposable needle 300. The disposable needle 300 is engaged with the end 204 of the handpiece 200. The end 204 is affixed to the case 202. On the case 202 is a switch 206 for activating the needle 300. Also illustrated in FIG. 2 are the power cable 210 and the irrigation tube 208.

Figure 3:
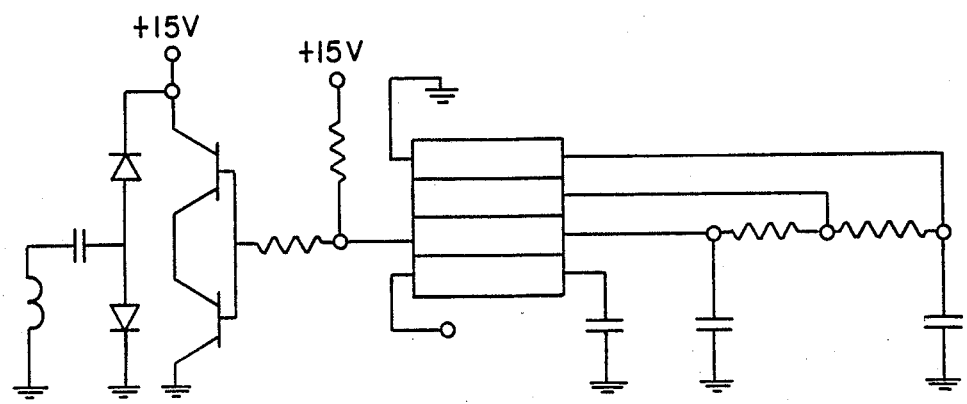
FIG. 3 illustrates a preferred embodiment of a schematic utilized in association with the console of the capsulectomy apparatus of the present invention.

FIG. 3 illustrates a presently preferred embodiment of an electrical circuit used in the console 100 of the present invention. As illustrated in the circuit of FIG. 3, the transducer 130 provides a resistance of 400 ohms.

Figure 4:
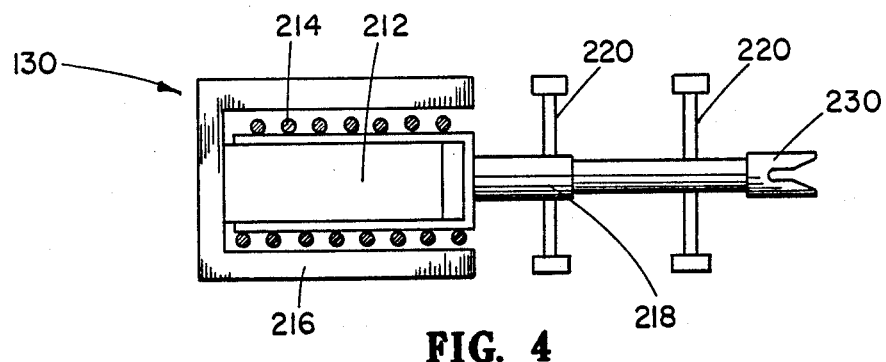
FIG. 4 is a representation of a preferred embodiment of the transducer mechanism within the handpiece of the capsulectomy apparatus of the present invention.

The transducer of the present invention is illustrated in its presently preferred embodiment in FIG. 4. The transducer 130 is similar to a "loud-speaker-type" moving coil motor. More particularly, the preferred embodiment of the transducer 130 comprises a cup 216 in which a coil 214 and a magnet 212 provide oscillation motion. The shaft 218 which is fixedly secured to the magnet 212 oscillates as does the magnet 212. The shaft 218 is kept in position within the handpiece 200 by the suspension members 220. Affixed to the end of the shaft 218 is the female actuator 230. Thus, as the magnet 212 vibrates, the shaft 218 vibrates and the female actuator 230 vibrates.

Figure 5:
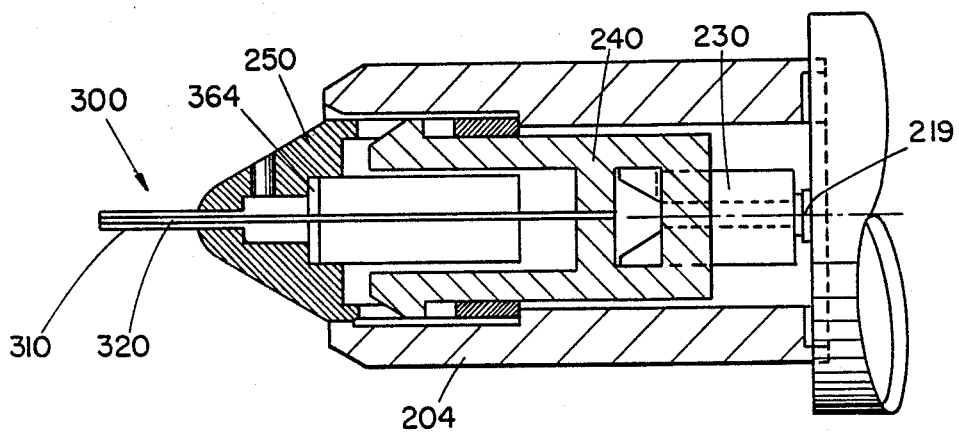
FIG. 5 is a sectional view of a preferred embodiment of a portion of the handpiece engaged with a portion of the needle of the capsulectomy apparatus of the present invention.

FIG. 5 illustrates the end portion of the handpiece 200 engaged with the needle 300 of the capsulectomy apparatus of the present invention. The primary components illustrated in FIG. 5 are the shaft 218 and the female actuator 230 of the handpiece 200 as well as the toggle 240, the end 250, the sleeve 310, the rod 320, and the fluid retainer diaphram 364 of the needle 300.

Figure 6:
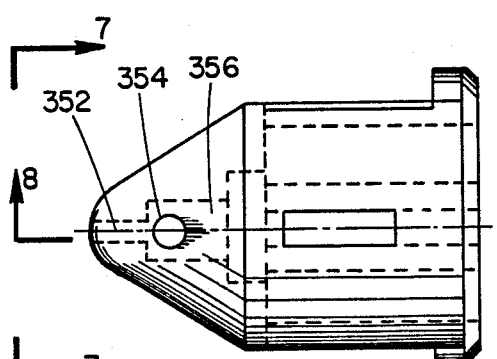
FIG. 6 is a sectional view of a preferred embodiment of the end/locking portion of the needle that secures to the handpiece of the capsulectomy apparatus of the present invention.

FIG. 6 is a sectional view of the end 350 which engages the handpiece 200 of the capsulectomy apparatus of the present invention. Of particular interest in FIG. 6 are the end channel 352, the irrigation channel 354, and the fluid chamber 356. The rod 320 of the needle 300 passes through the end channel 352 and the fluid chamber 356 into the rear portion of the end 350. The sleeve 310 is fixedly engaged with the end channel 352.

Figure 7:
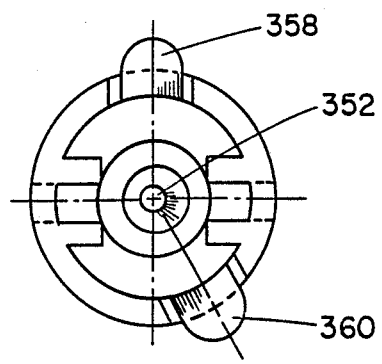
FIG. 7 is a cross-sectional view of the end/locking portion of the needle taken along section line 7—7 in FIG. 6.

FIG. 7 is a cross-sectional view taken along the section line 7—7 in FIG. 6. FIG. 7 illustrates the front portion of the end 350. Also, FIG. 7 illustrates the off-centered location of the first foot 358 relative to the second foot 360.

Figure 8:
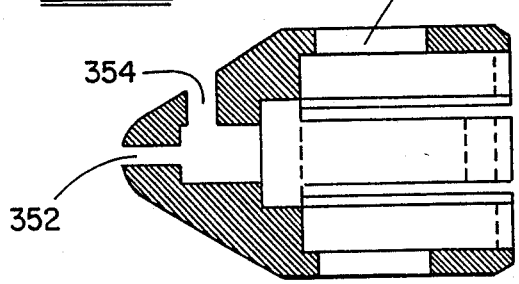
FIG. 8 is a cross-sectional view of the end/locking portion of the needle taken along section line 8—8 in FIG. 6.

FIG. 8 is a cross-sectional view taken along the section line 8—8 in FIG. 6 illustrating the end 350. FIG. 8 provides a center, cross-sectional view of the end 350. The needle channel 352 and the irrigation channel 354 are readily illustrated in FIG. 8. Also illustrated in FIG. 8 is the slot 362. The slot 362 is longitudinally disposed within the end 350. The slot 362 is disposed to form a rectangular channel through the central longitudinal axis of the end 350.

FIG. 9 illustrates the presently preferred embodiment of the toggle 340 which interacts with the end 350. The toggle 340 comprises the male end 342 and, disposed on the opposite end of the toggle 340, the first securing member 344 and the second securing member 346. The securing members 344 and 346 movably engage the end 350 within the slots 362.

FIG. 10 is a cross-sectional view of the toggle 340 taken along the section line 10—10 in FIG. 9 best illustrating the male end 342. Specifically, FIG. 10 illustrates the aperture 348 which accepts and secures the rod 320. Thus, as the toggle 340 moves in the slots 362 of the end 350, the rod 320 moves within the sleeve 310.

FIG. 11 is a cross-sectional view taken along section line 11—11 in FIG. 9 illustrating another perspective of the toggle 340.

FIG. 12 illustrates a presently preferred embodiment of the female actuator 230. The female actuator 230 comprises the driver end 232 and the securing members 234 which form a funnel.

FIG. 13 is a cross-sectional view taken along the section line 13—13 in FIG. 12 illustrating the female actuator 230 rotated 90 degrees from the position illustrated in FIG. 12. Upon rotating the female actuator 90 degrees, a securing channel 236 is formed. FIG. 14 is a cross-sectional view taken along section line 14—14 in FIG. 13.

FIG. 15 illustrates the use of the needle 300 within the eye. The needle 300 enters the eye at point C. As illustrated in FIG. 15, the head 330 of the needle 300 is actively cutting the lens B. The needle 300 is illustrated with the sleeve 310 and the rod 320 passing therethrough. Fixedly secured to and illustrated as a part of the rod 320 is the head 330. The head 330 is the active cutting member of the needle 300.

Figure 16:
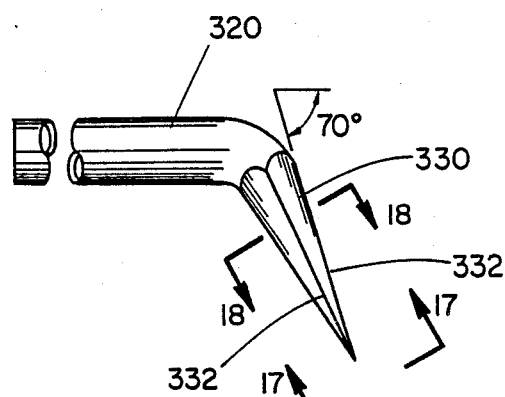
FIG. 16 is a exploded view of the end portion of the preferred embodiment of the rod associated with the needle of the capsulectomy apparatus of the present invention.

FIG. 16 is a blown-up illustration of a portion of the rod 320 and the head 330. Of particular importance in the present invention, is the angle of declanation of the central axis relating to the head 330 and rod 320. This angle is illustrated as approximately 70 degrees. However, a range of angles of declanation from approximately 70 to 135 degrees provides enhanced cutting characteristics. The head 330 is illustrated as having four cutting edges 332. Preferably, the head 330 can be configured to have from 2-5 cutting edges 332 for the currently performed ophthalmic procedures. However, the head 330 could be readily adopted with more than five (5) cutting edges 332.

Figure 17:
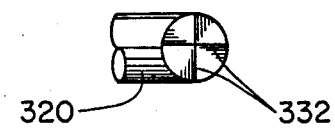
FIG. 17 is a cross-sectional view of the end portion of the preferred embodiment of the rod associated with the needle taken along section line 17—17 in FIG. 16.

FIG. 17 is a cross-sectional view taken along section line 17—17 of FIG. 16 which better illustrates the four cutting edges 332. The cutting edges are anglelarly specific based upon the number of edges 332 associated with the head 330 used, i.e., 2-5 edges 332 may be used.

Figure 18:
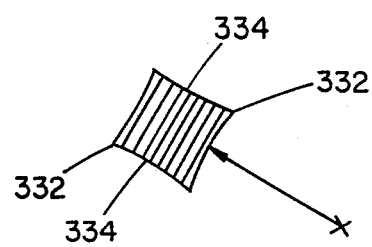
FIG. 18 is a cross-sectional view of the end portion of the preferred embodiment of the rod associated with the needle taken along section line 18—18 in FIG. 16.

FIG. 18 is a cross-sectional view taken along section line 18—18 in FIG. 16 illustrating the curvature associated with each cutting surface 334. Preferably, the cutting surfaces 334 have a radius of curvature of less than 0.05 inches. For the apparatus illustrated in FIGS. 15-18, the radius of curvature is approximately 0.307 inches for the four sided polyhedral structure of the head 330.

Figure 19:
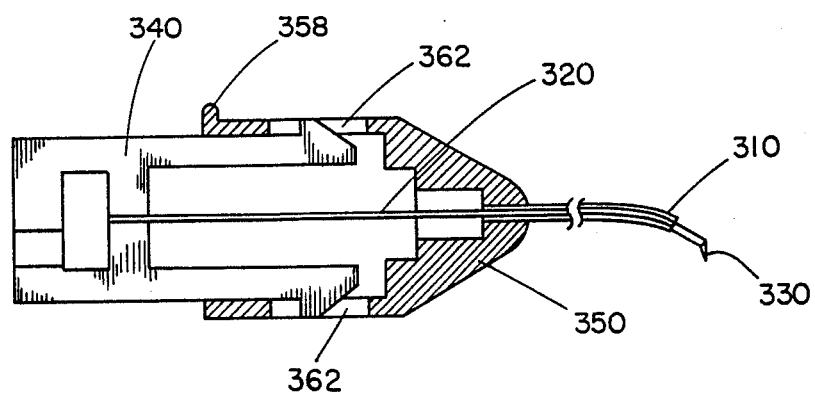
FIG. 19 is a sectional view of a preferred embodiment of the needle of the capsulectomy apparatus of the present invention.

FIG. 19 illustrates the needle 300 utilized in the capsulectomy apparatus of the present invention. The toggle 340 is movably affixed in the slot 62 of the end 350. The sleeve 310 is fixedly secured to the end 350. The rod 320 is fixedly secured to the toggle 340 adjacent to the securing channel 349. The rod 320 passes between the securing members 344 and 346 through the end 350, and through the sleeve 310 to extend out of the sleeve 310. The head 330 is affixed to the end of the rod 320 or is an extension thereof. As the toggle 340 is moved in the slot 362, the rod 320 moves within the end 350 and the sleeve 310 causing the head 330 to oscilate.

Figure 20:
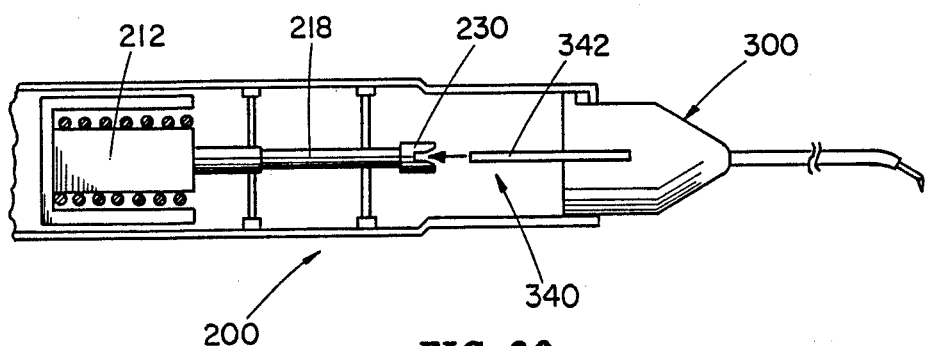
FIG. 20 is a sectional view of the needle being inserted into the handpiece illustrating the locking mechanism which removebly affixes the needle to the handpiece.

FIG. 20 illustrates the needle 300 being affixed to the handpiece 200. The female actuator 230 is affixed to the shaft 210 which is driven by the transducer apparatus within the handpiece 200. The male end 342 of the toggle 340 is moved into the funnel created by the securing members 234 and 236. The feet 358 and 360 on the end 350 slide into slots which prevent the male end 342 and female actuator 230 from being engaged improperly. After the male end 342 is completely engaged in the funnel of female actuator 230, the needle 300 can be rotate 90 degrees so that the first foot 258 and the second foot 260 lock into place to fixedly secure the needle 300 to the handpiece 200. The securing channel 236 of the female actuator 230 is wrapped around the male end 342 of the toggle 340. Similarly, the securing members 234 and 236 of the female actuator 230 have engaged the securing channel 349 of the toggle 340. Thus, as the needle 300 is rotated 90 degrees, the feet 358 and 360 removably engage the handpiece 200 to fixedly secure the needle 300. However, as the female actuator 330 is driven by the shaft 218, the rod 320 is oscilated within the sleeve 230 to cause the head 330 to provide a cutting action.

Figure 21A:
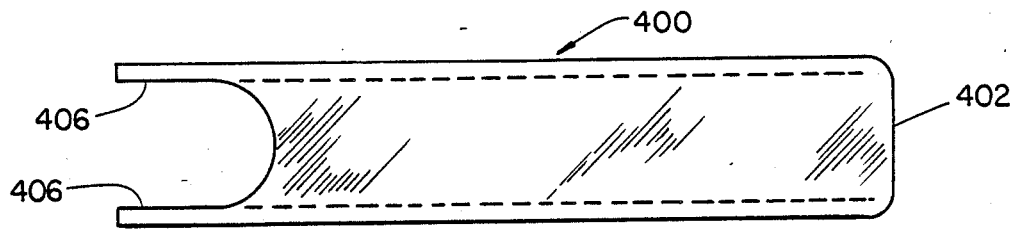
FIG. 21A illustrates a plan view of the preferred embodiment of the insertion tool used with the capsulectomy apparatus of the present invention.

FIG. 21A illustrates a plan view of the preferred embodiment of the insertion tool 400 used with the capsulectomy apparatus of the present invention. The insertion tool 400 is illustrated having a closed end 402 and remotely disposed therefrom an opened end 404. Associated with the opened end 404 are the extensions 406. The extensions 406 are linear extensions of the cylindrical sides of the insertion tool 400.

Figure 21B:
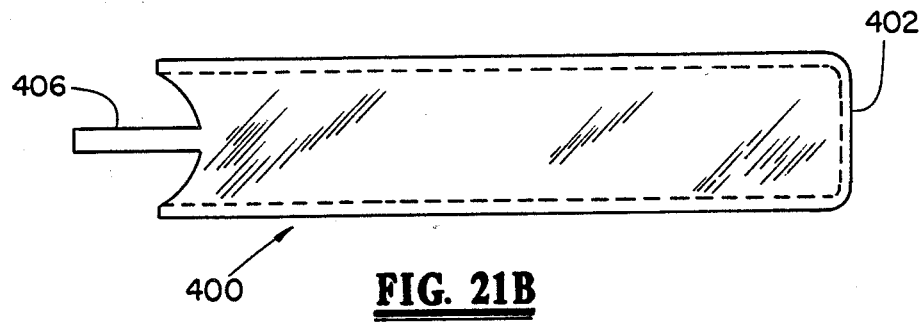
FIG. 21B illustrates an elevation view of the insertion tool illustrated in FIG. 21A as used with the capsulectomy apparatus of the present invention.

FIG. 21B illustrates an elevation view of the preferred embodiment of the insertion tool 400 as illustrated in FIG. 21A. Remote from the closed end 42 is the opened end 404 having associated therewith the extensions 406. The extensions 406 are illustrated with the lower extension lying directly under the upper extension and thus the lower extension 406 is out of view in FIG. 21B.

Figure 22:
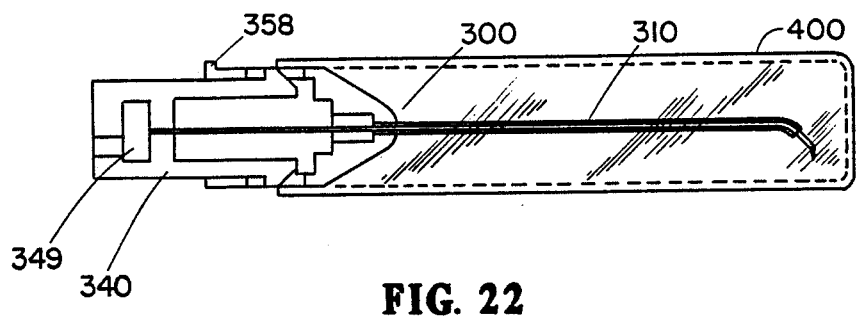
FIG. 22 is a sectional view illustrating the arrangement of the insertion tool to the needle prior to engaging the needle with the handpiece.

FIG. 22 is a section view illustrating the arrangement of the insertion tool 400 to the needle 300 prior to engaging the needle 300 with the hand piece 200 (the latter not illustrated in FIG. 22). The insertion tool 400 is illustrated engaged over the toggle 340 of the needle 300. The extensions 406 extending from the opened end 404 of the insertion tool 400 abuttedly engage the foot 358 associated with the toggle 340 of the needle 300.

It has been found that adequate cutting frequencies are between 50 and 300 Hz. Also, it has been found that the amplitude of motion of the rod 320 within the sleeve 310 caused by the movement of the actuator 230 is between 0.005 inches and 0.050 inches. It can be readily derived by one skilled in the art that differing frequencies and amplitudes of the motion may readily enhance the use of the present apparatus for different surgical techniques of cutting needs.

OPERATION

In operating the capsulectomy apparatus of the present invention, the handpiece 200 is connected to the console 100 via the power cable 210. The irrigation tube 208 attaches to the console 100 at the irrigation solenoid 128. Use of the irrigation tube 208 is optional and at the discretion of the operator. The console 100 requires power from readily available sources. Preferably, the console 100 is battery powered. The instrumentation associated with the capsulectomy apparatus of the present invention provides that the handpiece indicator 118 illuminates when the handpiece 200 is properly set and functional. The needle indicator 116 illuminates to notify the operator that the handpiece 200 and the needle 300 are properly set. The test button 112 runs for approximately three (3) seconds to determine if the capsulectomy apparatus is ready for operation. The internal circuit determines the presence of a spike on the wave form which indicates the unit is vibrating. The irrigation indicator 108 and the cutting indicator 106 provide visual or audible communications to the operator. The fault indicator 110 illuminates when the needle 300 or handpiece 200 are disengaged or the power fails or the needle 300 disengages.

When the console 100 is activated, power is supplied to the transducer 130 such that the shaft 218 drives the female actuator 230, the toggle 340 and the rod 330 within the sleeve 310 of the needle 300. Simultaneously, irrigation fluid enters the end 350 through the irrigation channel 354 for irrigating deep in the anterior chamber through hydrostatic pressure. The irrigation fluid is prevented from transfering into the main portion of the handpiece 200 by the fluid retainer diapham 364 (See FIG. 5). As the transducer 130 drives the rod 320, the cutting edges 332 and the cutting surfaces 334 of the head 330 cleanly and smoothly severe the lens B of the eye.

After the needle 300 has been used, it is readily removed and disgarded. Another needle is engaged with the handpiece 200. The needle can be readily engaged with the handpiece 200 using any device which readily displaces the toggle 340 to its most recessed position.

The sleeve 310 is inserted into the channel 352 such that the rod 320 removably engages the toggle 340. Thus, as the toggle 340 is activated by the female actuator 230 due to the vibrating shaft 218, the rod 320 longitudinally fluctuates for cutting the lens B of the eye.

An example of the types of surgery performed by the capsulectomy apparatus of the present invention is as follows:

A peretomeh performed at the superior 90 degree segment using a No. 11 sterrsharp blade. After the incision has been accurately placed, the surgeon takes the handpiece 200 from the nurse and depresses the handswitch or a footswitch. The flow of irrigation solution egresses a bottle suspended on an IV pole. The surgeon enters the anterior chamber at the incision site by rotating the handpiece 200 ninety degrees such that the blade is horizontal or parallel with the incision. The anterior chamber deepens and the surgeon then rotates the handpiece 200 ninety degrees back to the original position. The surgeon punctures the anterior lens with the needle capsule at any point. The handswitch or footswitch is then depressed to a second position which activates the cutting mechanism. The surgeon then guides the handpiece in such a fashion as to "draw" the desired shape capsulectomy in one continuous motion. The shape can be circular, ellipticial, D-shaped or any other shape depending on surgeon preference. The end result from this sequence of events is the production of a tag-free, free-floating, continuous, smooth, curvilinear anterior capsule flap with no stress on the zonules. The anterior capsule remaining will facilitate placement of an intraocular lens (IOL) in the capsular bag.

The head 330 must be in constant contact with the capsule to ensure a smooth cut. The needle 300 does not have to be perpenduclar to the plane of the capsule at all times as with prior known devices.

To remove the handpiece 200 from the eye, the needle 300 is rotated ninety degrees and withdrawn through the incision. A capsulectomy performed with this method can be accomplished within approximately 5 to 10 seconds.

What is claimed is:

1. A capsulectomy apparatus for faciliating a continuous, smooth, curvilinear, stress-free, tag-free, free-floating cut of the anterior capsule comprising:
   (a) a handpiece,
   (b) means for providing a source of power and lubricating fluids to said handpiece,
   (c) a disposable needle which is removably affixed to the handpiece for providing a continuous cutting mechanism for the capsulectomy apparatus, and
   (d) a locking mechanism for restricting the position of the disposable needle with respect to said handpiece to insure a continuous, smooth, curvilinear, stress-free, tag-free, free-floating cut of the anterior capsule, said locking mechanism comprises:
      (1) a toggle fixedly engaged with said disposable needle and having a securing channel therein, and
      (2) a driver fixedly engaged with said handpiece and having a toggle channel, the toggle channel of said driver for accepting said toggle for removably securing said disposable needle to said handpiece by rotating said toggle until the securing channel interlocks with the toggle channel.

2. A capsulectomy apparatus as defined in claim 1 wherein said handpiece comprises a vibratory oscilator for displacing the position of the needle for providing a continuous cutting mechanism.

3. A capsulectomy apparatus as defined in claim 2 wherein said vibratory oscilator comprises a magnet, a metalic coil surrounding said magnet, a charging device for providing an electric field to the magnet and coil for creating displacement forces between the magnet and the coil, and a shaft affixed to and moving in association with said coil for displacing the position of the needle for providing a continuous cutting mechanism.

4. A capsulectomy apparatus as defined in claim 1 wherein said disposable needle comprises an elongate portion and a polyhedron-shaped cutting head having concaved sides fixedly secured to said elongate portion.

5. A capsulectomy apparatus as defined in claim 4 wherein the concaved sides of said polyhedron-shaped cutting head have a radius of curvature of less than approximately 0.05 inches.

6. A capsulectomy apparatus as defined in claim 4 wherein said polyhedron-shaped cutting head deviates from said elongate portion of said disposable needle by from approximately 60 degrees to approximately 135 degrees.

7. A capsulectomy apparatus as defined in claim 4 wherein said polyhedron-shaped cutting head oscilates at a frequency of from approximately 50 Hz to approximately 300 Hz.

8. A capsulectomy apparatus as defined in claim 4 wherein said polyhedron-shaped cutting head oscilates having an amplitude of motion of from approximately 0.005 inches to approximately 0.05 inches.

9. A capsulectomy apparatus as defined in claim 4 wherein said polyhedron-shaped cutting head has four sides and the concaved sides of said polyhedron-shaped cutting head have a radius of curvature of approximately 0.037 inches.

10. A capsulectomy apparatus as defined in claim 1 further comprising an insertion member for protecting said disposable needle during transportation and for providing that said disposable needle correctly engages said handpiece for ensuring the proper operation of the capsulectomy apparatus.

11. A capsulectomy apparatus for faciliating a continuous, smooth, curvilinear, stress-free, tag-free, free-floating cut of the anterior capsule comprising:
   (a) a handpiece comprising a vibratory oscilator for displacing the position of the needle for providing a continuous cutting mechanism, and vibratory oscilator comprises a magnet, a metalic coil surrounding said magnet, a charging device for providing an electric field to the magnet and coil for creating displacement forces between the magnet and the coil, and a shaft affixed to and moving in association with said coil for displacing the position of the needle for providing a continuous cutting mechanism.
   (b) means for providing a source of power and lubricating fluids to said handpiece.
   (c) a disposable needle which is removably affixed to the handpiece for providing a continuous cutting mechanism for the capsulectomy apparatus, said disposable needle comprises an elongate portion and a polyhedron-shaped cutting head having four concaved sides fixedly having a radius of curvature of approximately 0.037 inches secured to said elongate portion wherein the concaved sides of said polyhedron-shaped cutting head have a radius of curvature of less than approximately 0.05 inches, and said polyhedron-shaped cutting head deviates from said elongate portion of said disposable needle by from approximately 60 degrees to approximately 135 degrees and oscilates at a frequency of from approximately 50 Hz to approximately 300 Hz having an amplitude of motion of from approximately 0.005 inches to approximately 0.05 inches, and (d) a locking mechanism for restricting the position of the disposable needle with respect to said handpiece to insure a continuous, smooth, curvilinear, stress-free, tag-free, free-floating cut of the anterior capsule, said locking mechanism comprises:

(1) a toggle fixedly engaged with said disposable needle and having a securing channel therein, and (2) a driver fixedly engaged with said handpiece and having a toggle channel, the toggle channel of said driver for accepting said toggle for removably securing said disposable needle to said handpiece by rotating said toggle until the securing channel interlocks with the toggle channel, and (e) an insertion member comprising a cylindrical member having an enclosed end and an open end such that the open end has extensions protruding therefrom for guiding said disposable needle to actively engage said handpiece for ensuring the proper affixation of said disposable needle with said handpiece and the proper operation of the capsulectomy apparatus.

* * * * *